United States Patent
Tran

(10) Patent No.: US 10,460,076 B2
(45) Date of Patent: Oct. 29, 2019

(54) SUPERIMPOSED VERIFIED PHOTO WITH ORDER OR REQUEST

(71) Applicant: SOHI, LLC, Clearwater, FL (US)

(72) Inventor: Thi Tran, Clearwater, FL (US)

(73) Assignee: SOHI, LLC, Clearwater, FL (US)

( * ) Notice: Subject to any disclaimer, the term of this patent is extended or adjusted under 35 U.S.C. 154(b) by 744 days.

(21) Appl. No.: 14/460,962

(22) Filed: Aug. 15, 2014

(65) Prior Publication Data

US 2015/0051921 A1 Feb. 19, 2015

Related U.S. Application Data

(60) Provisional application No. 61/866,697, filed on Aug. 16, 2013.

(51) Int. Cl.

| | |
|---|---|
| *G06F 19/00* | (2018.01) |
| *G16H 30/40* | (2018.01) |
| *G16H 30/20* | (2018.01) |
| *G16H 30/00* | (2018.01) |
| *G16H 10/60* | (2018.01) |

(52) U.S. Cl.
CPC ......... *G06F 19/321* (2013.01); *G16H 10/60* (2018.01); *G16H 30/00* (2018.01); *G16H 30/20* (2018.01); *G16H 30/40* (2018.01)

(58) Field of Classification Search
CPC ...... G06Q 50/22; G06Q 50/24; G06F 19/321; G16H 30/40; G16H 30/20; G16H 30/00; G16H 10/60
USPC ........................................................ 705/2–3
See application file for complete search history.

(56) References Cited

U.S. PATENT DOCUMENTS

| | | | | |
|---|---|---|---|---|
| 2006/0025658 A1* | 2/2006 | Newman | ........... | A61B 3/0058 600/301 |
| 2009/0310836 A1* | 12/2009 | Krishnan | ........... | G06T 7/0012 382/128 |
| 2011/0231205 A1* | 9/2011 | Letts | ........... | G06F 19/321 705/3 |
| 2012/0209093 A1* | 8/2012 | Olszewski | ........... | A61B 6/032 600/310 |
| 2012/0330876 A1* | 12/2012 | Bryce | ........... | G16H 15/00 706/47 |
| 2013/0039550 A1* | 2/2013 | Blum | ........... | G06T 7/0014 382/128 |

FOREIGN PATENT DOCUMENTS

WO      WO 2013144186 A1 * 10/2013 ............. A61B 5/441

* cited by examiner

*Primary Examiner* — Eliza A Lam
(74) *Attorney, Agent, or Firm* — Tucker Ellis LLP; Carlos Garritano

(57) ABSTRACT

Systems and methods of the invention relate to aggregating digital data for a patient during an examination at a private physician office environment, wherein the digital data is associated with a data file for the patient. A physician can utilize a device to capture an image of a patient or a portion of a patient, wherein the image relates to a condition or an area of medical concern based on the physician's opinion. In particular, the image can be superimposed onto a generic human body shape such that a precise location of the area of medical concern is identified by a marker and further the image.

10 Claims, 6 Drawing Sheets

SUPERIMPOSED VERIFIED PHOTO WITH ORDER OR REQUEST

CROSS-REFERENCE TO RELATED APPLICATIONS

This application claims priority to U.S. Provisional Application Ser. No. 61/866,697, filed Aug. 16, 2013, entitled "SUPERIMPOSED VERIFIED PHOTO WITH ORDER OR REQUEST", the entirety of which is herein incorporated by reference.

BACKGROUND OF THE INVENTION

1. Field of the Invention

This application relates generally to capturing digital images during a patient visit at a private physician office environment.

2. Description of Related Art

Diagnostic laboratories provide diagnostic testing services to physicians and can often be located remotely and/or organizationally separate from private offices maintained by the physicians. Often, a patient is provided with an order request from a physician during an office visit. The patient travels to a laboratory location with the order request to provide samples on which diagnostic tests are performed in accordance with the order request. Results of the diagnostic tests are sent back to the physician. Alternatively, the samples can be acquired at the physician's office and subsequently couriered to the laboratory along with the order request. Such samples, however, are not conventionally linked to a location of the body from which the samples are acquired.

BRIEF SUMMARY OF THE INVENTION

A simplified summary is provided herein to help enable a basic or general understanding of various aspects of exemplary, non-limiting embodiments that follow in the more detailed description and the accompanying drawings. This summary is not intended, however, as an extensive or exhaustive overview. Instead, the sole purpose of the summary is to present some concepts related to some exemplary non-limiting embodiments in a simplified form as a prelude to the more detailed description of the various embodiments that follow.

According to an embodiment, a system is described that includes a computing device comprising a display and an input device and being further associated with a camera; and a data store configured to store at least digital images, patient data, and marker information. In an example, the computing device is configured to control the camera to capture a digital image of a portion of a patient, to receive a input via the input device indicative of a selection of a location of a human body, to generate marker information associating the location of the human body selected and the digital image captured. In addition, the computing device is further configured to store the digital image and marker information in associated with the patient data in the data store.

In another embodiment, a method is described that includes capturing a digital image of a portion of a patient. The method further includes displaying an image of a human body to a physician, and receiving input indicative of a selection of an area of the human body. In addition, the method can include associating the digital image of the portion of the patient with the area of the human body selected by the input. Further, the method can include displaying the image of the human body to the physician with a marker superimposed thereon at a location corresponding to the area of the human body selected.

In an embodiment, a method is provided that includes at least the following steps: capturing a digital image of a portion of a patient, wherein the portion of the patient includes at least one of a skin condition or a skin disease; displaying a human body image to a physician; receiving a portion of information that identifies the patient; selecting an area on the human body image; displaying a zoomed view of the area on the human body image; receiving an input from the physician that is a location on the zoomed view of the area; corresponding the digital image to the input; storing the corresponding digital image and the input with the portion of information that identifies the patient; and creating a marker that illustrates the location on the human body image, wherein the marker corresponds to a physical location on the patient where the physician captures the digital image.

These and other embodiments are described in more detail below.

BRIEF DESCRIPTION OF THE DRAWINGS

Reference is made to the accompanying drawings in which particular embodiments and further benefits of the invention are illustrated as described in more detail in the description below, in which.

DETAILED DESCRIPTION OF THE INVENTION

Figure 1:
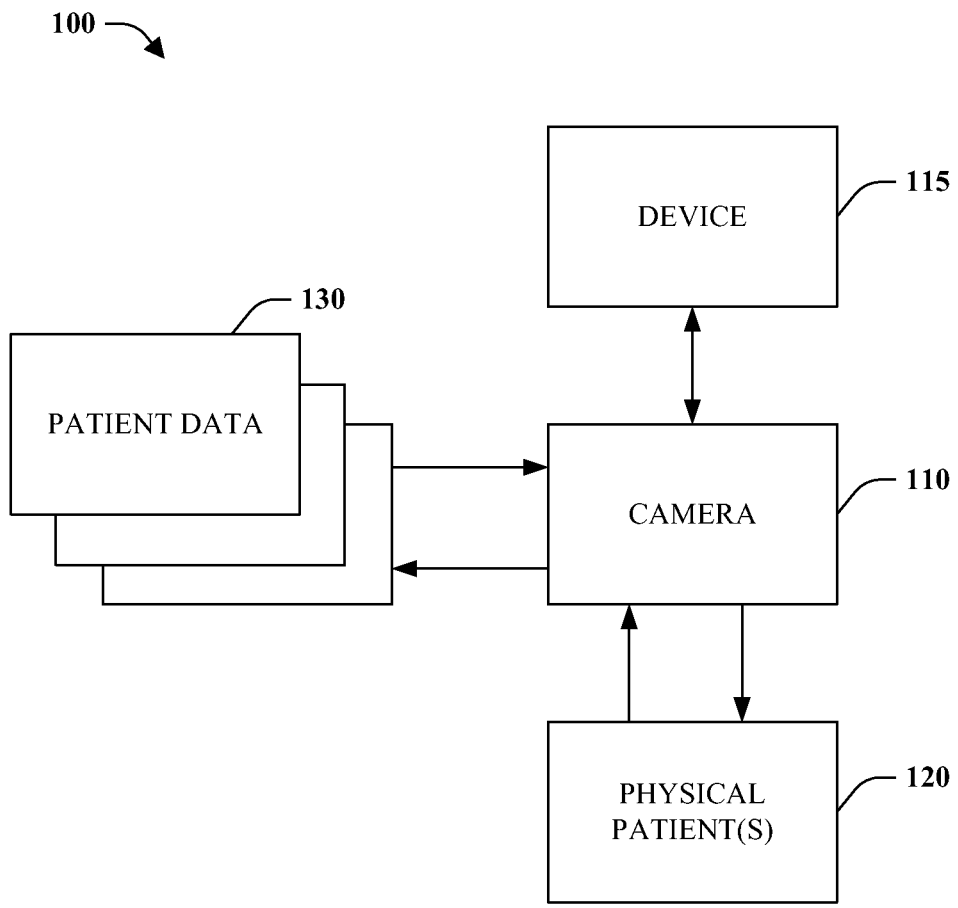
FIG. 1 is an illustration of an embodiment of a system for capturing a digital image of a patient to include with an electronic file for the patient.

Embodiments of the invention relate to methods and systems for aggregating digital data for a patient during an examination at a private physician office environment, wherein the digital data is associated with a data file for the patient. A physician can utilize a device to capture an image of a patient or a portion of a patient, wherein the image relates to a condition or an area of medical concern based on the physician's opinion. In particular, the image can be superimposed onto a generic human body shape such that a precise location of the area of medical concern is identified by a marker and further the image.

With reference to the drawings, like reference numerals designate identical or corresponding parts throughout the several views. However, the inclusion of like elements in different views does not mean a given embodiment necessarily includes such elements or that all embodiments of the invention include such elements.

The term "component" as used herein can be defined as a portion of hardware, a portion of software, or a combination thereof. A portion of hardware can include at least a processor and a portion of memory, wherein the memory includes an instruction to execute.

FIG. 1 is a system 100 for capturing a digital image of a patient to include with an electronic file for the patient. The system 100 can include a camera 110 that is configured to capture a digital image of a portion of a patient, wherein the digital image is representative of a physical location on the patient. For instance, the digital image can be of a dermatological condition of the patient such as, but not limited to, a skin disease or a skin condition. The camera 110 can be a separate device (as depicted), incorporated into a device 115, or a combination thereof. By way of example and not limitation, the device 115 can be, but is not limited to being, any suitable device that controls a digital camera (e.g., camera 110), a computer, a desktop machine, a tablet, a portable device, a portable digital assistant, a smartphone, a laptop, a computing device, a porting gaming device, a game console, a device that can access the Internet, a kiosk, a terminal, a display, a surface computing device, smart glass, a surface that interacts with a user's motion or touch, and the like. The camera 110 allows a physician to capture an image of a physical location on a physical patient 120, wherein the physical location includes a skin condition, skin disease, or an area of concern based on a physician's diagnosis or physical exam.

The captured image of the physical location can be incorporated with patient data 130, wherein the patient data is a tabulation or collection of information related to the patient. For instance, the captured digital image can be captured with information such as, but not limited to, a date of appointment, a physician that examined the patient, an office location, a test to perform on a biopsy, a procedure to perform on a biopsy of the patient, a laboratory to send an order request to perform a test or procedure, a previous procedure or test, a previous medical condition, a physician diagnosis, among others. In general, the camera 110 allows the physician to capture a digital image of a patient while the patient is physically at an appointment, exam, checkup in an office environment of the physician.

In an embodiment, an office environment can be a dermatology office in which one or more physicians examine and provide care to patients in the medical field of at least dermatology. The office environment can include one or more physicians, wherein each patient can include a respective chart, file, and/or patient data. It is to be appreciated that a chart, a file, or patient data 130 for a patient can be any suitable collection of information (e.g., hard copy, soft copy, a combination thereof) collected from the patient directly and/or indirectly from at least one of an interview of the patient, an examination of the patient, an insurance company of the patient, a parent of the patient, a guardian of the patient, an insurance card, a transfer file from another physician, an electronic communication from the patient, and/or any other suitable source that provides patient information. The collection of information can be tabulated or collected as an electronic file for the patient (e.g., patient data 130). For instance, a hard copy of a file for a patient can be electronically scanned to create an electronic file. Following such example, additional information collected or identified during an examination can be appended to the electronic file during intake with an electronic device. In another example, an electronic file for a patient can be gathered and aggregated via an electronic device (e.g., tablet, computer, handheld, among others). It is to be appreciated and understood that the intake of patient data or aggregation of patient data can include a conversion of hard copy files or charts, electronic intake of patient data, electronic intake for files or charts, and/or any suitable combination thereof.

In an embodiment, the laboratory can be a facility or environment that can perform one or more tests for a patient at a request of the office environment and/or the physician via an order. For instance, the request can be an order request from a physician to perform a test or a procedure. In a particular example, the order request can be from a physician to perform a pathology test on a biopsy sample obtained from a patient.

In an embodiment, a physician can add information to an electronic file for a patient, wherein the information can be, for instance, a digital image, an annotation, a digital image of a patient that captures a dermatological condition on skin, among others. The physician can determine that a test should be performed for the patient and such request for the test or procedure can include the added information captured during an exam by the physician. It is to be appreciated that the physician can transmit patient data 130 as well as any captured data (e.g., digital image of the portion of the patient). For instance, the physician can determine that a first test can include information A, B, and C, whereas a second test can include information B, D, F, and G. It is to be appreciated that any suitable data can be defined to include in the order request to a testing facility or a laboratory. According to an embodiment, order requests, digital images captured and processed as described herein, as well as other information related to patients, conditions, providers, medical history, etc. can be transmitted to the laboratory as an electronic data package. For example, co-pending application Ser. No. 14/460,959 filed Aug. 15, 2014, incorporated herein by reference, describes one exemplary technique for facilitating communication between a physician office and a laboratory.

In another embodiment, the laboratory can be a facility that fills a prescription. For instance, a physician at the office environment can meet a patient and communicate an order request to the laboratory that fills a prescription for the patient, wherein the order request and other information is handled. In this particular embodiment, a captured image and other information can be transmitted by the physician to ensure a chain-of-custody from the office environment to the laboratory and from the laboratory to the office environment. For instance, the captured digital image can be embedded and included with an order to fill a prescription for the patient.

It is to be appreciated that the system 100 can be deployed in any suitable operating system environment based on, for instance, being implemented with a browser, wherein a browser or web browser is a portion of software that allows information resources on the World Wide Web to be retrieved, presented, and/or traversed. The system 100 can be employed based on an Hyper Text Markup Language (HTML) tag structure that allows for a device and/or operating system agnostic deployment. For instance, the system 100 can be implemented on a mobile platform, a desktop operating system, any suitable browser that handles HTML tags, among others.

Figure 2:
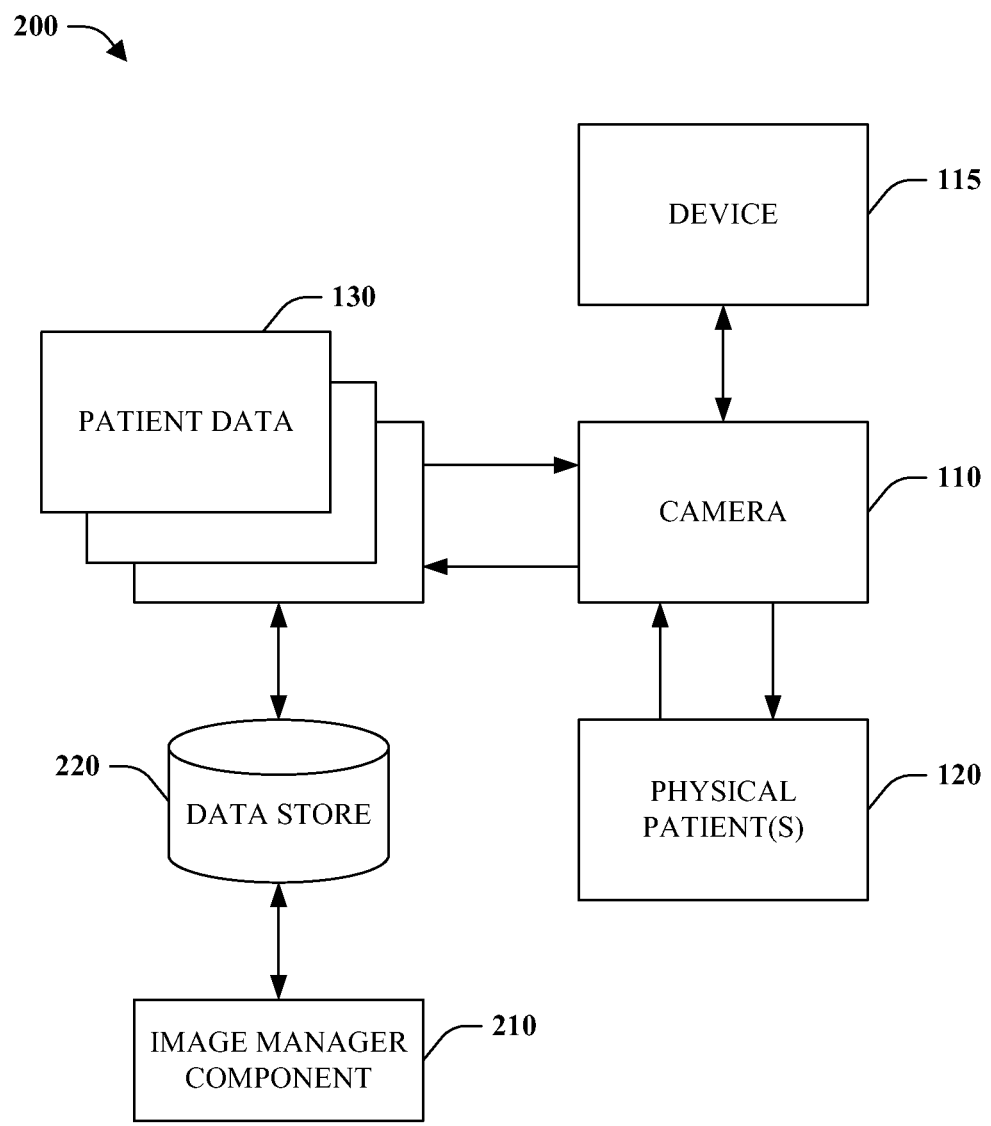
FIG. 2 is an illustration of an embodiment of a system for managing images captured for a patient.

FIG. 2 is a system 200 for managing images captured for a patient. The system 200 can further include an image manager component 210 that is configured to manage digital images captured for a patient by a physician during a physical exam or checkup. For instance, the physician can capture digital images related to areas of concern related to a skin condition, a skin disease, an location on the patient that is related to a potential health risk, among others. Upon capturing of an image, the image manager component 210 can be configured to incorporate such captured image with an electronic file or patient data 130 such that the digital image is part of the patient file history. Moreover, the image manager component 210 can append the patient data 130 to include information collected during a physical exam such as, but not limited to, test performed, diagnosis information, laboratory to send a biopsy, a location of an area of which the digital image relates, a date and/or time of an appointment for which the digital image was captured, a physician performing the physical exam, patient identification information (e.g., date of birth, social security number, patient number, insurance information, among others), type of skin condition, type of skin disease, procedure history, test results, procedure results, order request for a test or procedure, invoice information, among others.

The image manager component 210 can aggregate various information from a physician and/or during a physical examination of the patient. Moreover, such information is tabulated and can be displayed to a physician based on selectable criteria. For instance, a physician can sort or display information for a patient based on a period of time. In another example, the physician can display digital images collected by physician A. In another example, the physician can display digital images for a patient that has corresponding biopsy results from a laboratory. By way of example and not limitation, the selectable criteria can be a data, a time, a patient name, a patient reference identification, a type of skin condition, a type of skin disease, a test performed, a measurement of at least one of the skin condition or the skin disease, a biopsy result, a physician that diagnosed the patient, a physician office location, among others.

It is to be appreciated that the image manager component 210 can be implemented on the device 115, wherein the device can be, but is not limited to being, any suitable device that includes a digital camera (e.g., camera 110), a computer, a desktop machine, a tablet, a portable device, a portable digital assistant, a smartphone, a laptop, a computing device, a porting gaming device, a game console, a device that can access the Internet, a kiosk, a terminal, a display, a surface computing device, smart glass, a surface that interacts with a user's motion or touch, and the like.

The data store 220 can store media from the system 200 such as, but not limited to, patient identification, patient personal information, order requests, templates for requests, template data for patient intake, office environment information (e.g., source information), laboratory environment information, addresses, shipping details, electronic payment information, cryptology information, passwords, authentication information, digital images, data related to the capturing of the digital image (e.g., date, time, patient, skin condition, location, etc.), and the like. It is to be appreciated that the data store 220 can be, for example, either volatile memory or nonvolatile memory, or can include both volatile and nonvolatile memory. The data store 220 of the subject systems and methods is intended to comprise, without being limited to, these and other suitable types of memory. In addition, it is to be appreciated that the data store 220 can be a server, a database, a hard drive, a flash drive, an external hard drive, a portable hard drive, a cloud-based storage, a solid-state drive, a distributed storage system, and the like. The data store 220 can further be a local data store, a remote data store, a cloud-based data store, or a combination thereof.

Figure 3:
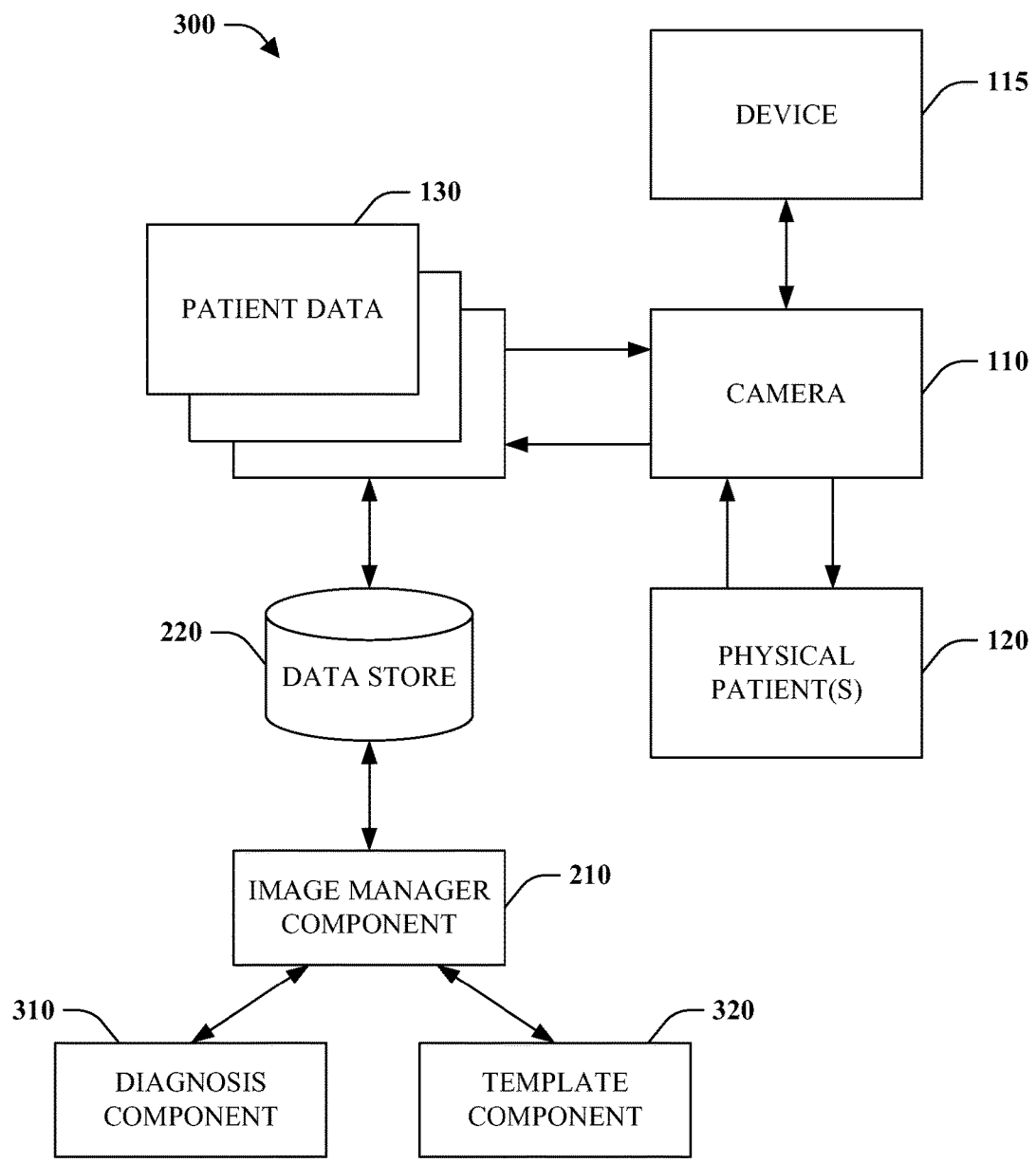
FIG. 3 is an illustration of an embodiment of a system for diagnosing a patient.

FIG. 3 is a system 300 for diagnosing a patient. The system 300 can include a diagnosis component 310 that is configured to evaluate historic data collected for a patient and infer or determine a medical condition, and in particular, a dermatological condition for the patient. For example, historic data can include medical history data, previous digital images processed according to the techniques described herein information, as well as electronic data packages exchanged between one or more laboratories and one or more physicians as described in co-pending application Ser. No. 14/460,959 filed Aug. 15, 2014. According to this example, the diagnosis component 310 can readily identify a condition as an established condition or a recurrence condition.

In particular, the system 300 and/or diagnosis component 310 can collect information (e.g., test results, digital images, biopsy results, etc.) for a patient over a period of time, wherein such information can be evaluated to reveal or identify particular patterns or medical symptoms. Moreover, the diagnosis component 310 can collect information for a particular patient to determine or infer a diagnosis as well as use information for other patients to determine or infer a diagnosis. In other words, the diagnosis component 310 can utilize patient specific data as well as information from other patients to determine a diagnosis. Further, the patterns between multiple patients can be evaluated and/or identified in order to infer or determine a diagnosis. For instance, the diagnosis component 310 can utilize image analysis techniques and neural networks to identify conditions from the digital images.

In an embodiment, the system 300 can allow a physician or an office environment to customize a template for patient data intake with a template component 320, wherein the intake can include patient data, procedures, a type of medicinal practice (e.g., dermatology, orthopedics, pediatrics, among others), physician defined information, among others. The template component 320 can include customizable inputs for data from a physician such that the inputs are for data received from a patient during an exam. For instance, the template component 320 can provide customization that relates to location, subjective, objective, assessment, plan of treatment, among others.

It is to be appreciated that the diagnosis component 310 can be a stand-alone component (as depicted), incorporated into the image manager component 210, incorporated into the camera 110, incorporated into the device 115, and/or any suitable combination thereof. Moreover, the template component 320 can be a stand-alone component (as depicted), incorporated into the image manager component 210, incorporated into the camera 110, incorporated into the device 115, and/or any suitable combination thereof.

Figure 4:
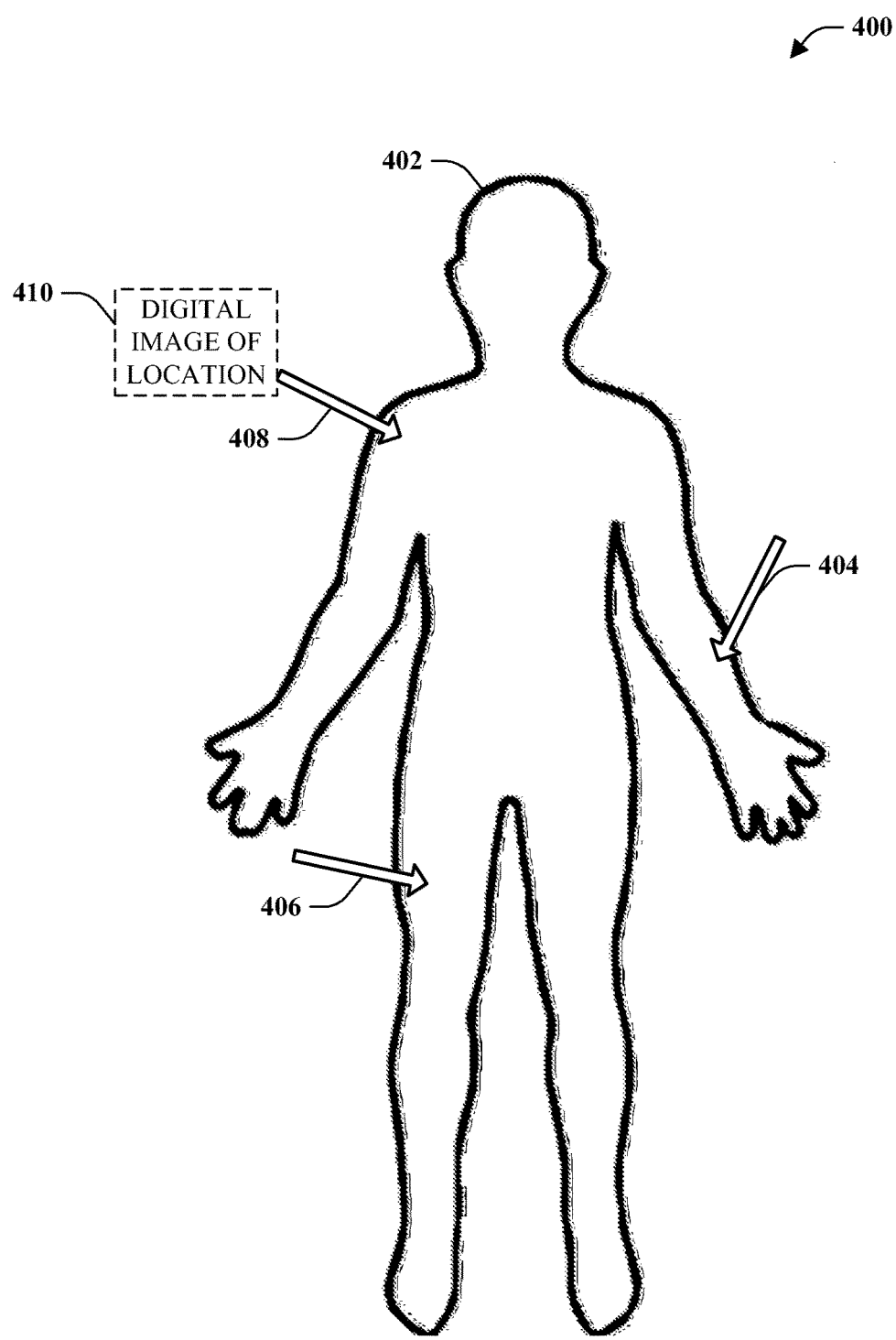
FIG. 4 is an illustration of display screen utilized to embed a captured digital image.

FIG. 4 is a display screen 400 utilized to embed a captured digital image. The display screen 400 that is rendered on a device (e.g., device 115). The display screen 400 can illustrate a human body image 402 that is, for instance, an outline of a human body. It is to be appreciated that any suitable image of a body or human body can be utilized and the human body image 402 is solely for example. For instance, the human body image 402 can be, but is not limited to, a full body photo of the particular patient, a silhouette of the patient, a silhouette of a human body, a 3-dimensional image, a color image, among others. The display screen 400 illustrates a main view of the human body image 402, wherein a user or physician can zoom to a particular area therefrom. For instance, the physician can zoom to a closer view of a portion of the human body image 402 to provide a more detailed view of an area of the image 402. By zooming in, the physician can have a view with more detail so as to allow precise location of a marker indicating a digital image captured. It is to be appreciated that any suitable number of zoom levels can be provided with the subject innovation.

The display screen 400 illustrates one or more markers and in particular, marker 404, 406, and 408. The markers can be a graphical icon or displayed marker that indicates a digital image has been captured at a particular location, wherein the particular location is representative of a physical location on a patient. It is to be appreciated that the markers 404, 406, and 408 illustrated can be sorted or organized based on selectable criteria in order to facilitate displaying information collected during patient intake at one or more physician visits or appointments. Moreover, it is to be appreciated that the markers 404, 406, 408 can appear or disappear based on an input from the physician. For instance, a mouse hover or a touchscreen input can allow a marker to display or not be displayed.

The display screen 400 illustrates markers 404, 406, and 408 as well as a digital image of location 410. It is to be appreciated that the digital image of location is a digital image captured with a device for the particular patient and is representative of a location on the patient's physical body. Thus, the digital image of location 410 is a photo or digital image of the patient's right shoulder and can illustrate a skin condition or a skin disease. Moreover, the digital image of location 410 can be displayed on the human body image 402 as well as various zoom in levels of the human body image 402. In another embodiment, the digital image of location 410 can be not displayed until a zoom level is achieved. In still another embodiment, the digital image of location 410 can be not displayed until a user or physician input to a marker is received. For instance, each marker can correspond to a respective digital image of location, wherein such digital image is displayed upon physician input (e.g., click, touch input on touchscreen, voice command, hand gesture, movement of device, among others) on the display screen 400.

It is to be appreciated that the device 115 can be, but is not limited to being, a computer, a desktop machine, a tablet, a portable device, a portable digital assistant, a smartphone, a laptop, a computing device, a porting gaming device, a game console, a device that can access the Internet, a kiosk, a terminal, a display, a surface computing device, smart glass, a surface that interacts with a user's motion or touch, a machine with a portable camera, and the like.

The aforementioned systems, components, (e.g., device 115, camera 110, image manager component 210, diagnosis component 310, template component 320, among others), and the like have been described with respect to interaction between several components and/or elements. It should be appreciated that such devices and elements can include those elements or sub-elements specified therein, some of the specified elements or sub-elements, and/or additional elements. Further yet, one or more elements and/or sub-elements may be combined into a single component to provide aggregate functionality. The elements may also interact with one or more other elements not specifically described herein.

Figure 5:
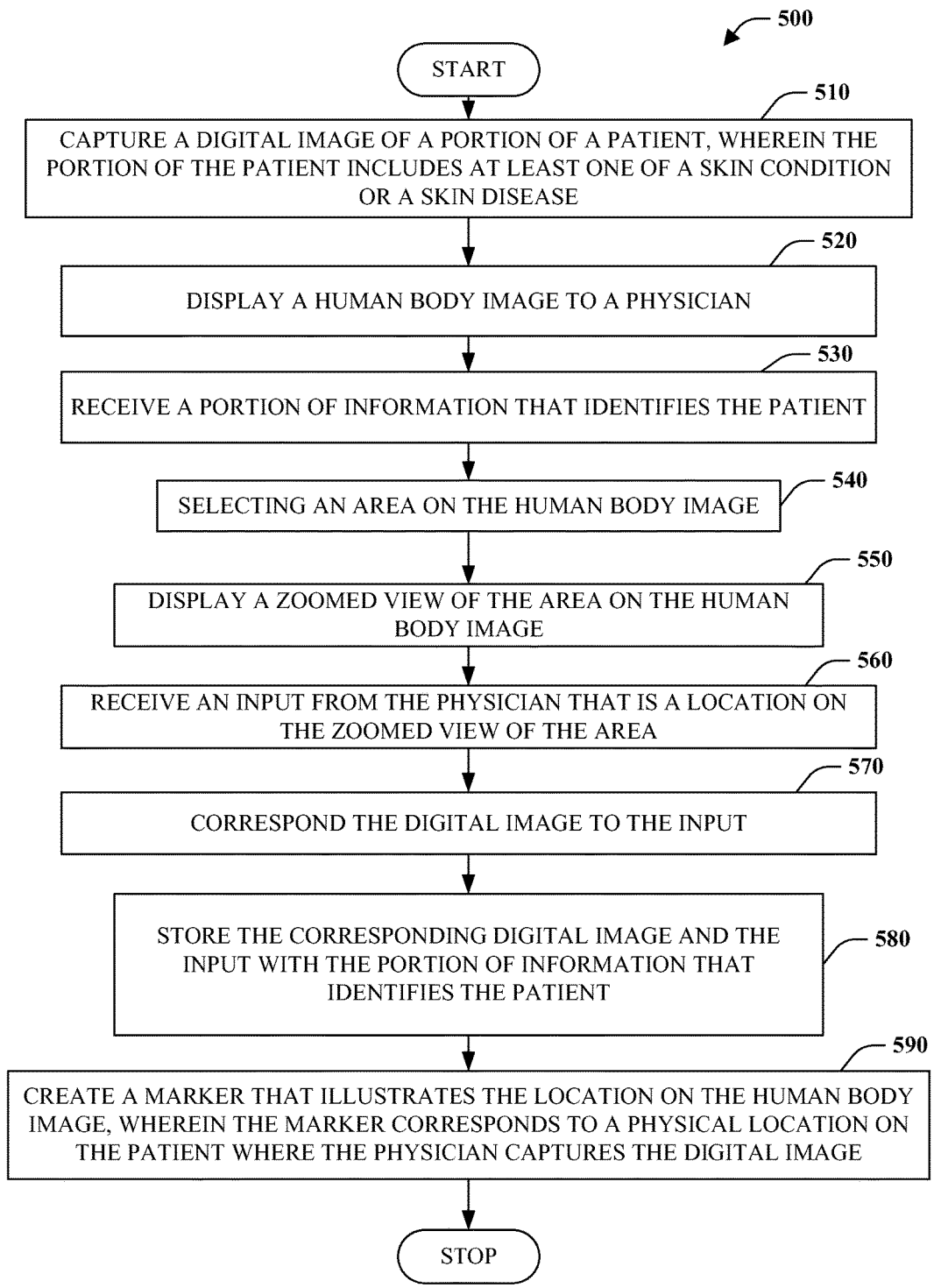
FIG. 5 illustrates a flow chart of an embodiment of a method for incorporating a digital image of a patient to an image of a human body to correspond to a location of a skin condition of the patient.

In view of the exemplary devices and elements described supra, methodologies that may be implemented in accordance with the disclosed subject matter will be better appreciated with reference to the flow chart of FIG. 5, among others. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks may be required to implement the methods described hereinafter.

FIG. 5 illustrates a method 500 that facilitates incorporating a digital image of a patient with an electronic file or chart of the patient. At reference numeral 510, a digital image of a portion of a patient can be captured, wherein the portion of the patient includes at least one of a skin condition or a skin disease. At reference numeral 520, a human body image can be displayed to a physician. At reference numeral 530, a portion of information that identifies the patient can be received. At reference numeral 540, an area on the human body image can be selected. At reference numeral 550, splaying a zoomed view of the area on the human body image can be displayed. At reference numeral 560, an input from the physician can be received that is a location on the zoomed view of the area. At reference numeral 570, the digital image can be corresponded to the input. At reference numeral 580, the corresponding digital image and the input with the portion of information that identifies the patient can be stored. At reference numeral 590, a marker that illustrates the location on the human body image can be created, wherein the marker corresponds to a physical location on the patient where the physician captures the digital image.

In an embodiment, the method can include receiving at least one of a type of skin condition, a type of skin disease, a date, a time, a measurement of at least one of the skin condition or the skin disease, a test to perform on at least one of the skin condition or the skin disease, or a patient reference identification. In an embodiment, the method can include displaying the human body image and at least one of the marker or the digital image. In an embodiment, the method can include receiving a selectable criteria to organize at least one of the marker or the digital image and displaying the human body image and at least one of the marker or the digital image based on the selectable criteria. In an embodiment, the selectable criteria is at least one of a data, a time, a patient name, a patient reference identification, a type of skin condition, a type of skin disease, a test performed, a measurement of at least one of the skin condition or the skin disease, a biopsy result, a physician that diagnosed the patient, or a physician office location.

In an embodiment, the method can include taking a biopsy of the portion of the patient that is captured with a digital image. In an embodiment, the method can include embedding a portion of data with the digital image, wherein the portion of data is at least one of a procedure to perform on a biopsy of the portion of a patient, a test to perform on a biopsy of the portion of the patient, a location on the patient of where the digital image corresponds, or a laboratory site that is to perform at least one of the test or the procedure on the biopsy. In an embodiment, the method can include communicating an order to a laboratory for at least one of a test or a procedure on the biopsy, wherein the order includes the digital image and the portion of data embedded therein.

As used herein, the terms "component" and "system," as well as forms thereof are intended to refer to a computer-related entity, either hardware, a combination of hardware and software, software, or software in execution. For example, a component may be, but is not limited to being, a process running on a processor, a processor, an object, an instance, an executable, a thread of execution, a program, and/or a computer. By way of illustration, both an application running on a computer and the computer can be a component. One or more components may reside within a process and/or thread of execution and a component may be localized on one computer and/or distributed between two or more computers.

The word "exemplary" or various forms thereof are used herein to mean serving as an example, instance, or illustration. Any aspect or design described herein as "exemplary" is not necessarily to be construed as preferred or advantageous over other aspects or designs. Furthermore, examples are provided solely for purposes of clarity and understanding and are not meant to limit or restrict the claimed subject matter or relevant portions of this disclosure in any manner. It is to be appreciated a myriad of additional or alternate examples of varying scope could have been presented, but have been omitted for purposes of brevity.

As used herein, the term "inference" or "infer" refers generally to the process of reasoning about or inferring states of the system, environment, and/or user from a set of observations as captured via events and/or data. Inference can be employed to identify a specific context or action, or can generate a probability distribution over states, for example. The inference can be probabilistic—that is, the computation of a probability distribution over states of interest based on a consideration of data and events. Inference can also refer to techniques employed for composing higher-level events from a set of events and/or data. Such inference results in the construction of new events or actions from a set of observed events and/or stored event data, whether or not the events are correlated in close temporal proximity, and whether the events and data come from one or several event and data sources. Various classification schemes and/or systems (e.g., support vector machines, neural networks, expert systems, Bayesian belief networks, fuzzy logic, data fusion engines . . . ) can be employed in connection with performing automatic and/or inferred action in connection with the claimed subject matter. For instance, the systems and methods described herein can be monitored and dermatological diagnostics can be inferred based on collected patient data on a per patient model or as a collective set of patients. An individual patient data over time can be evaluated to infer particular diagnosis in dermatology. Moreover, more than one patient information can be utilized to identify a diagnosis for a particular patient.

Furthermore, to the extent that the terms "includes," "contains," "has," "having" or variations in form thereof are used in either the detailed description or the claims, such terms are intended to be inclusive in a manner similar to the term "comprising" as "comprising" is interpreted when employed as a transitional word in a claim.

Figure 6:
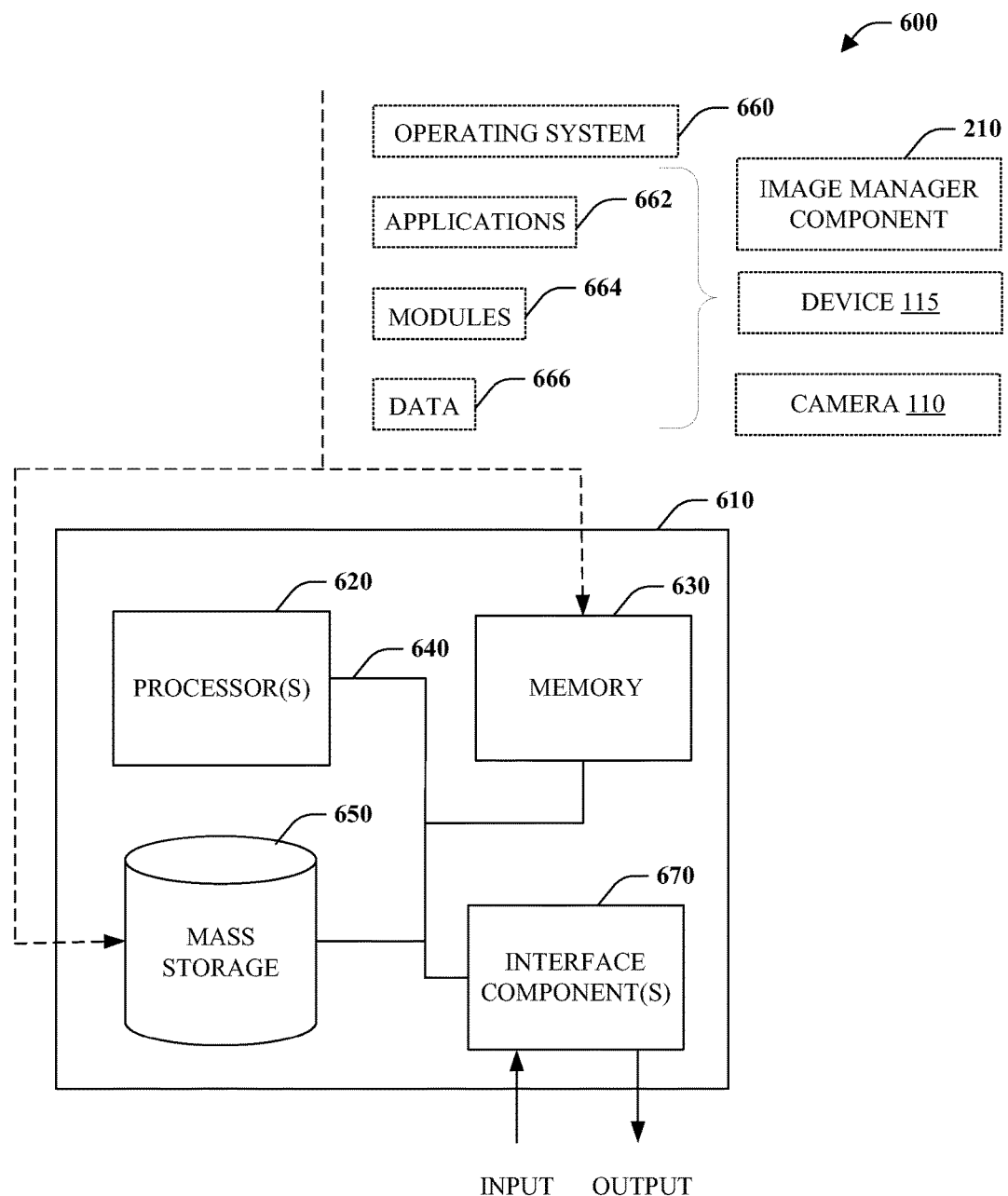
FIG. 6 is a schematic block diagram illustrating a suitable operating environment for aspects of the subject disclosure.

In order to provide a context for the claimed subject matter, FIG. 6 as well as the following discussion are intended to provide a brief, general description of a suitable environment in which various aspects of the subject matter can be implemented. The suitable environment, however, is only an example and is not intended to suggest any limitation as to scope of use or functionality.

While the above disclosed system and methods can be described in the general context of computer-executable instructions of a program that runs on one or more computers, those skilled in the art will recognize that aspects can also be implemented in combination with other program modules or the like. Generally, program modules include routines, programs, components, data structures, among other things that perform particular tasks and/or implement particular abstract data types. Moreover, those skilled in the art will appreciate that the above systems and methods can be practiced with various computer system configurations, including single-processor, multi-processor or multi-core processor computer systems, mini-computing devices, mainframe computers, as well as personal computers, hand-held computing devices (e.g., personal digital assistant (PDA), portable gaming device, smartphone, tablet, Wi-Fi device, laptop, phone, among others), microprocessor-based or programmable consumer or industrial electronics, and the like. Aspects can also be practiced in distributed computing environments where tasks are performed by remote processing devices that are linked through a communications network. However, some, if not all aspects of the claimed subject matter can be practiced on stand-alone computers. In a distributed computing environment, program modules may be located in one or both of local and remote memory storage devices.

With reference to FIG. 6, illustrated is an example general-purpose computer 610 or computing device (e.g., desktop, laptop, server, hand-held, programmable consumer or industrial electronics, set-top box, game system . . . ). The computer 610 includes one or more processor(s) 620, memory 630, system bus 640, mass storage 650, and one or more interface components 670. The system bus 640 communicatively couples at least the above system components. However, it is to be appreciated that in its simplest form the computer 610 can include one or more processors 620 coupled to memory 630 that execute various computer executable actions, instructions, and or components stored in memory 630.

The processor(s) 620 can be implemented with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any processor, controller, microcontroller, or state machine. The processor(s) 620 may also be implemented as a combination of computing devices, for example a combination of a DSP and a microprocessor, a plurality of microprocessors, multi-core processors, one or more microprocessors in conjunction with a DSP core, or any other such configuration.

The computer 610 can include or otherwise interact with a variety of computer-readable media to facilitate control of the computer 610 to implement one or more aspects of the claimed subject matter. The computer-readable media can be any available media that can be accessed by the computer 610 and includes volatile and nonvolatile media, and removable and non-removable media. By way of example, and not limitation, computer-readable media may comprise computer storage media and communication media.

Computer storage media includes volatile and nonvolatile, removable and non-removable media implemented in any method or technology for storage of information such as computer-readable instructions, data structures, program modules, or other data. Computer storage media includes, but is not limited to memory devices (e.g., random access memory (RAM), read-only memory (ROM), electrically erasable programmable read-only memory (EEPROM) . . . ), magnetic storage devices (e.g., hard disk, floppy disk, cassettes, tape . . . ), optical disks (e.g., compact disk (CD), digital versatile disk (DVD) . . . ), and solid state devices (e.g., solid state drive (SSD), flash memory drive (e.g., card, stick, key drive . . . ) . . . ), or any other medium which can be used to store the desired information and which can be accessed by the computer 610.

Communication media typically embodies computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

Memory 630 and mass storage 650 are examples of computer-readable storage media. Depending on the exact configuration and type of computing device, memory 630 may be volatile (e.g., RAM), non-volatile (e.g., ROM, flash memory . . . ) or some combination of the two. By way of example, the basic input/output system (BIOS), including basic routines to transfer information between elements within the computer 610, such as during start-up, can be stored in nonvolatile memory, while volatile memory can act as external cache memory to facilitate processing by the processor(s) 620, among other things.

Mass storage 650 includes removable/non-removable, volatile/non-volatile computer storage media for storage of large amounts of data relative to the memory 1030. For example, mass storage 650 includes, but is not limited to, one or more devices such as a magnetic or optical disk drive, floppy disk drive, flash memory, solid-state drive, or memory stick.

Memory 630 and mass storage 650 can include, or have stored therein, operating system 660, one or more applications 662, one or more program modules 664, and data 666. The operating system 660 acts to control and allocate resources of the computer 610. Applications 662 include one or both of system and application software and can exploit management of resources by the operating system 660 through program modules 664 and data 666 stored in memory 630 and/or mass storage 650 to perform one or more actions. Accordingly, applications 662 can turn a general-purpose computer 610 into a specialized machine in accordance with the logic provided thereby.

All or portions of the claimed subject matter can be implemented using standard programming and/or engineering techniques to produce software, firmware, hardware, or any combination thereof to control a computer to realize the disclosed functionality. By way of example and not limitation, the device 115, the camera 110, the image manager component 210, or portions thereof, can be, or form part, of an application 662, and include one or more modules 664 and data 666 stored in memory and/or mass storage 650 whose functionality can be realized when executed by one or more processor(s) 620.

In accordance with one particular embodiment, the processor(s) 620 can correspond to a system on a chip (SOC) or like architecture including, or in other words integrating, both hardware and software on a single integrated circuit substrate. Here, the processor(s) 620 can include one or more processors as well as memory at least similar to processor(s) 620 and memory 630, among other things. Conventional processors include a minimal amount of hardware and software and rely extensively on external hardware and software. By contrast, an SOC implementation of processor is more powerful, as it embeds hardware and software therein that enable particular functionality with minimal or no reliance on external hardware and software. For example, the device 115, the camera 110, the image manager component 210, and/or associated functionality can be embedded within hardware in a SOC architecture.

The computer 610 also includes one or more interface components 670 that are communicatively coupled to the system bus 640 and facilitate interaction with the computer 610. By way of example, the interface component 670 can be a port (e.g., serial, parallel, PCMCIA, USB, Fire Wire . . . ) or an interface card (e.g., sound, video . . . ) or the like. In one example implementation, the interface component 670 can be embodied as a user input/output interface to enable a user to enter commands and information into the computer 610 through one or more input devices (e.g., pointing device such as a mouse, trackball, stylus, touch pad, keyboard, microphone, joystick, game pad, satellite dish, scanner, camera, other computer . . . ). In another example implementation, the interface component 670 can be embodied as an output peripheral interface to supply output to displays (e.g., CRT, LCD, plasma . . . ), speakers, printers, and/or other computers, among other things. Still further yet, the interface component 670 can be embodied as a network interface to enable communication with other computing devices (not shown), such as over a wired or wireless communications link.

In the specification and claims, reference will be made to a number of terms that have the following meanings. The singular forms "a", "an" and "the" include plural referents unless the context clearly dictates otherwise. Approximating language, as used herein throughout the specification and claims, may be applied to modify a quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Moreover, unless specifically stated otherwise, a use of the terms "first," "second," etc., do not denote an order or importance, but rather the terms "first," "second," etc., are used to distinguish one element from another.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances the modified term may sometimes not be appropriate, capable, or suitable. For example, in some circumstances an event or capacity can be expected, while in other circumstances the event or capacity cannot occur—this distinction is captured by the terms "may" and "may be."

This written description uses examples to disclose the invention, including the best mode, and also to enable one of ordinary skill in the art to practice the invention, including making and using a devices or systems and performing incorporated methods. The patentable scope of the invention is defined by the claims, and may include other examples that occur to one of ordinary skill in the art. Such other examples are intended to be within the scope of the claims if they have structural elements that do not differentiate from the literal language of the claims, or if they include equivalent structural elements with insubstantial differences from the literal language of the claims.

What is claimed is:

1. A system, comprising:
a physician computing device comprising a display and an input device, the computing device being further associated with a camera;
a data store configured to store at least digital images, patient data, and marker information; and
a hub computing device,
wherein the physician computing device is configured to control the camera to capture a digital image of a portion of a patient, to receive an input via the input device indicative of a selection of a location of a human body, to generate marker information associating the location of the human body selected and the digital image captured, and control acquisition and storage of the patient data,
wherein the physician computing device is further configured to:
receive input data corresponding to the patient data in accordance with a customizable template;
store the digital image and marker information in association with the patient data in the data store;
output an image of the human body to the display with a marker superimposed thereon, the marker being displayed at the location of the human body selected;
receive input via the input device indicative of a selection of the marker superimposed on the image of the human body; and
output the digital image captured via the camera in association with the image of the human body in response to the input received,
embed the digital image with an electronic file patient information to create an electronic dermatology package;
communicate, to the hub computer device, the electronic dermatology package, and an order request, wherein the order request relates to a test to be performed at a laboratory; and
receive, from the hub computer device, the electronic dermatology package with the personal information and test results,
wherein the physician computing device is further configured to determine a condition of the patient associated with the digital image based at least in part on the patient data, the digital image, information related to other patients, and the test results,
wherein the hub computing device is configured to:
remove personal information that identifies the patient from the communication electronic dermatology package and the order request;
communicate, to an associated laboratory system, the order request and the electronic dermatology package without the personal information;
receive, from the associated laboratory system, test results;
restore the personal information to the electronic dermatology package and add the personal information that identifies the patient to the test result; and
communicate, to the physician computer device, the electronic dermatology package with the personal information and the test results.

2. The system of claim 1, wherein patient data, the marker information, and the digital image are included in an electronic data package that further includes information related to a condition of the patient, a provider treating the patient, a laboratory providing pathology services, and the test results.

3. A method, comprising:
receiving, by a physician computing device, patient information, wherein the patient information is acquired in accordance with a customizable template and a portion of information that identifies a patient;
capturing, by the physician computing device via a camera, a digital image of a portion of the patient, wherein the portion of the patient imaged includes a condition;
displaying, by the physician computing device, a representation of a human body image;
receiving, by the physician computing device, a first input indicative of a selection on the representation of the human body corresponding to an area on the human body;
displaying, by the physician computing device, a zoomed view of the representation of the human body corresponding to the area on the human body selected with the first input;
receiving, by the physician computing device, a second input indicative of a selection of a location within the zoomed view of the area;
storing, by the physician computing device, the digital image in association with marker information specifying the location on the human body together with the portion of patient information that identifies the patient; and
generating, by the physician computing device, a user interface that includes a representation of the human body with at least one marker superimposed on the representation that corresponds to the location on the human body captured by the digital image, wherein the user interface is responsive to a third input indicative of a selection of a marker to display an image associated therewith;
embedding, by the physician computing device, the digital image of the portion of the patient with the patient information to create an electronic dermatology package;
communicating, from the physician computing device to a hub computing device, the electronic dermatology package and an order request indicating a test to be performed at a laboratory;
removing, by the hub computing device, personal information that identifies the patient from the electronic dermatology package and the order request;
communicating, from the hub computing device to a laboratory system, the order request and the electronic dermatology package without the personal information;
receiving, at the hub computing device from the laboratory system, test results from the laboratory;
restoring, by the hub computing device, the personal information to the electronic dermatology package and adding the personal information associated with the patent to the test results; and
communicating, by the hub computing device to the physician computing device, the electronic dermatology package with the personal information and the test results; and
inferring, by the physician computing device, the condition of the patient associated with the digital image based at least in part on the patient information, the digital image, information related to other patients, and the test results.

4. The method of claim 3, further comprising receiving, by the physician computer device, at least one of a type of skin condition, a type of skin disease, a date, a time, a measurement of at least one of the skin condition or the skin disease, a test to perform on at least one of the skin condition or the skin disease, or a patient reference identification.

5. The method of claim 3, further comprising:
   receiving selectable criteria by which marker information and digital images are organized in order to filter stored images and marker information; and
   displaying the user interface including the representation of the human body with one or more markers superimposed thereon that correspond to the selectable criteria.

6. The method of claim 3, further comprising taking a biopsy of the portion of the patient that is captured with a digital image.

7. The method of claim 3 wherein the digital image corresponding to the marker is superimposed over the zoomed view of the area on the human body image in response to receiving the second input.

8. The system of claim 1 wherein the image of the human body is a generic human body shape.

9. The system of claim 1 wherein the image of the human body is a silhouette of the human body.

10. The method of claim 5, the selectable criteria is at least one of a data, a time, a patient name, a patient reference identification, a type of skin condition, a type of skin disease, a test performed, a measurement of at least one of the skin condition or the skin disease, a biopsy result, a physician that diagnosed the patient, or a physician office location.

* * * * *